United States Patent [19]

Miura et al.

[11] Patent Number: 4,894,487

[45] Date of Patent: Jan. 16, 1990

[54] PREPARATION PROCESS OF 4-(4-HYDROXYPHENYL)-CYCLOHEXANOL

[75] Inventors: Tohru Miura; Masayuki Furuya; Teruyuki Nagata, all of Ohmuta, Japan

[73] Assignee: Mitsui Toatsu Chemicals, Incorporated, Tokyo, Japan

[21] Appl. No.: 228,186

[22] Filed: Aug. 4, 1988

[30] Foreign Application Priority Data

Aug. 14, 1987 [JP] Japan ................................. 62-201939

[51] Int. Cl.$^4$ ........................ C07C 35/23; C07C 35/27
[52] U.S. Cl. .................................. 568/832; 568/715; 568/743; 568/822
[58] Field of Search ............... 568/721, 730, 743, 822, 568/807, 715, 832

[56] References Cited

U.S. PATENT DOCUMENTS 3,697,606 10/1972 Freudewald et al. ............. 260/620
4,723,046 2/1988 Nagata et al. ....................... 568/730

FOREIGN PATENT DOCUMENTS 0251614 6/1986 European Pat. Off. ............ 568/743
62128 4/1983 Japan ................................ 568/743

OTHER PUBLICATIONS

Patent Abstracts of Japan, vol. 7, No. 151, (Jul. 2, 1983), (C-174), 1296 for Japanese Published Patent Application No. 58-62128.
Chemische Berichte, 22, 335.
J. Organic Chemistry, 34, 1160 (1969).

*Primary Examiner*—Werren B. Lone
*Attorney, Agent, or Firm*—Fisher, Christen & Sabol

[57] ABSTRACT

This invention relates to a novel preparation process of 4-(4-hydroxyphenyl)-cyclohexanol, which comprises subjecting 4-(4-hydroxphenyl)-3-cyclohexen-1-ol to reduction. 4-(4-Hydroxyphenyl)-cyclohexanol is a compound useful as a monomer for liquid crystalline polyesters and the like.

6 Claims, No Drawings

PREPARATION PROCESS OF 4-(4-HYDROXYPHENYL)-CYCLOHEXANOL

BACKGROUND OF THE INVENTION a. Field of the Invention:

This invention relates to a novel preparation process of 4-(4-hydroxyphenyl)-cyclohexanol, which is a compound usual as a monomer for liquid crystalline polyesters and the like.

b. Description of the Prior Art:

As processes for the synthesis of 4-(4-hydroxyphenyl)-cyclohexanol, there have been proposed the following three processes only.

(1) After monomethylation of 4,4'-biphenol, hydrogenation is effected to obtain 4-(4-methoxyphenyl)-cyclohexanone. It is then oxidized into 4-(4-methoxyphenyl)-cyclohexanone with a chromium compound, followed by demethylation with aluminum bromide so as to synthesize 4-(4-hydroxyphenyl)-cyclohexanone. It is thereafter reduced with sodium boron hydride. [Chem. & Ind., 1437 (1958)].

(2) 4,4'-Biphenol is reacted with hydrogen in the presence of a Raney-nickel catalyst, thereby synthesizing 4-(4-hydroxyphenyl)-cyclohexanol [J. Am. Chem Soc., 76, 1733 (1954)].

(3) 4-(4-Tosyloxycyclohexyl)-phenol is subjected to decomposition in the presence of a potassium tert.butoxide catalyst [Chem. & Ind., 1437 (1958)].

The above-described conventional processes are accompanied by drawbacks such as many steps are required, the yield is low and expensive raw materials are required, so that the resultant 4-(4-hydroxyphenyl)-cyclohexanol naturally and unavoidably becomes extremely expensive. The above-described conventional processes are hence by no means satisfactory.

SUMMARY OF THE INVENTION

An object of this invention is to provide an industrial preparation process which can obtain highpurity 4-(4-hydroxyphenyl)-cyclohexanol in a high yield.

This invention therefore provides a novel process for the preparation of 4-(4-hydroxyphenyl)cyclohexanol, which comprises subjecting 4-(4-hydroxyphenyl-3-cyclohexen-1-ol to reduction.

DETAILED DESCRIPTION OF THE INVENTION 4-(4-Hydroxyphenyl)-3-cyclohexen-1-ol, which is employed as a starting material in this invention, is a compound provided by the present inventors. It can be obtained by subjecting 4,4-bis(4-hydroxyphenyl)cyclohexanol to a decomposition reaction under heat. A patent application has already been made on this compound (U.S. patent application Ser. No. 178301).

In addition, 4,4-bis(4-hydroxyphenyl)-cyclohexanol is also a compound provided by the present inventors. It can be obtained by reacting 4-hydroxycyclohexanone and phenol in the presence of an acidic catalyst. Another patent application has already been made on this compound (U.S. Pat. No. 4,723,046).

On the other hand, 4-hydroxycyclohexanone can be obtained by a method known per se in the art, for example, by reducing hydroquinone or oxidizing 1,4-cyclohexanediol.

In the present invention, 4-(4-hydroxyphenyl)-3-cyclohexen-1-ol obtained as described above is subjected to reduction so as to obtain 4-(4-hydroxyphenyl)-cyclohexanol.

For the reduction of 4-(4-hydroxyphenyl)-3-cyclohexen-1-ol, it is possible to use, besides hydrogen, a metal such as sodium or lithium, a metal hydride such as diisobutylaluminum hydride or organotin hydride, a metal-hydrogen complex such as lithium aluminum hydride, sodium aluminum hydride, lithium boron hydride or sodium boron hydride, or a reducing reagent such as diboran, an alkylboran, hydrazine, a diimide or a phosphorus compound. Electrolytic reduction is also effective. Of these, catalytic reduction making use of hydrogen is preferred when operability, costs and the like are taken into consideration. No particular limitation is imposed on the catalyst for the catalytic reduction so long as it is a known hydrogenation catalyst. As illustrative examples of the catalyst, may be mentioned nickel catalysts such as Raney-nickel, reduced nickel and nickel carried on various carriers such as diatomaceous earth, alumina, pumice, silica gel and acid clay; cobalt catalysts such as Raney-cobalt, reduced cobalt and cobalt-carrier catalysts; copper catalysts such Raney-copper, reduced copper and copper-carrier catalysts; palladium catalysts such as palladium black, palladium oxide, colloidal palladium, palladium-carbon, palladium-barium sulfate, palladium-magnesium oxide, palladium-calcium oxide and palladium-alumina; platinum group catalysts including platinum catalysts such as platinum black, colloidal platinum, platinum oxide, platinum sulfide and platinum-carbon, rhodium catalysts such as colloidal rhodium, rhodium-carbon and rhodium oxide, and ruthenium catalysts; rhenium catalysts such as dirhenium heptoxide and rhenium-carbon; copper chromate catalyst; molybdenum oxide catalyst; vanadium oxide catalyst; tungsten oxide catalyst; silver catalysts.

Among these catalysts, Raney-nickel catalyst, palladium catalysts and platinum catalysts are preferred. More preferred are palladium catalysts such as palladium-carbon.

The hydrogenation catalyst may be used usually in a range of 0.0001–0.1 gram atom, preferably, 0.0005–0.01 gram atom as the metal element or elements of the catalyst per mole of 4-(4-hydroxyphenyl)-3-cyclohexen1-ol.

A solvent is usually employed in the reaction of the process according to this invention. A compound resistant to reduction under the reaction conditions is chosen as the solvent.

Illustrative examples of the solvent may include aqueous solvents such as water and caustic water; alcohols such as methanol, ethanol, n-propyl alcohol, isopropyl alcohol, butyl alcohol, ethylene glycol, diethylene glycol, propylene glycol, triethylene glycol and glycerin, hydrocarbons such as benzene, toluene, xylene, cumene, ethylbenzene and cymene; nitriles such as acetonitrile and propionitrile; esters such as ethyl acetate and n-butyl acetate; ether such as tetrahydroran, dioxane and diethylene glycol monomethyl ether; organic polar solvents such as 1,3-dimethyl-2-imidazolidinone, N-methylpyrrolidone and dimethylformamide; and acids such as acetic acid.

Among these, the most preferred solvents are alcohol solvents such as methanol. The solvent may be used generally in an amount 5-20 times by weight the amount of 4-(4-hydroxyphenyl)-3-cyclohexen-1-ol.

In the process according to this invention, the reaction may be carried out generally at a temperature of 0°–100° C. with 20°–60° C. being preferred. The yield drops at reaction temperatures higher than 100° C., because side reactions occur at such high temperatures.

When the reduction in the process according to this invention is conducted as catalytic reduction making use of hydrogen, the reduction may be performed at a hydrogen pressure of 5 kg/cm²G or lower, preferably 2 kg/cm²G or lower, more preferably atmospheric pressure. A high pressure requires expensive facilities and cannot be recommended accordingly. In some instances, hydrogen may be used in a form diluted with a gaseous diluent such as nitrogen, helium, argon or carbon dioxide.

4-(4-Hydroxyphenyl)-cyclohexanol formed by the reaction of the process according to this invention can be obtained after completion of the reaction, for example, by filtering off the catalyst and then distilling the solvent.

4-(4-Hydroxyphenyl)-cyclohexanol thus obtained is pure white and has a high purity, and does not require any further purification for ordinary applications. If it is necessary to obtain it with a still higher purity, it may be purified by a conventional method such as recrystallization.

EXAMPLE

Preparation of 4,4-bis(4-hydroxyphenyl)cyclohexanol:

A reaction was conducted following the procedure described in Example 1 of Japanese Patent Application No. 185221/1986. Namely, 22.4 g (0.20 mole) of 4-hydroxycyclohexanone was dissolved in 188.4 g (2.0 moles) of phenol. HCl gas was bubbled at 40° C. to react them. After completion of the reaction, the reaction mixture was poured into a two-layer solvent composed of 500 ml of toluene and 200 ml of water, followed by thorough sludging at room temperature. crystals were collected by filtration and then dried under reduced pressure, thereby obtaining 64.9 g of phenol adducts of 4,4-bis(4-hydroxyphenyl)cyclohexanol. Purity: 98%. Purity-converted yield: 84% based on 4-hydroxycyclohexanone.

Preparation of 4-(4-hydroxyphenyl)-3-cyclohexen-1-ol:

The phenol adducts of 4,4-bis(4-hydroxyphenyl) cyclohexanol obtained as described above were reacted in toto in a manner similar to that described in Example 1 of Japanese Patent Application No. 89890/1987. Namely, the phenol adducts of 4,4-bis(4-hydroxyphenyl)cyclohexanol were added as a whole to a mixture of 100 ml of 1,3-dimethyl-2-imidazolidinone and 1 ml of a 50% aqueous solution of caustic soda. They were then reacted at 200°-220° C. for 3 hours. In the course of the reaction, the reaction system was depressurized after an elapsed time of 0.5 hour so as to draw phenol-containing 1,3-dimethyl-2-imidazolidinone out of the system. After completion of the reaction, the residue in the reaction tank was dissolved in caustic water and then acidified with hydrochloric acid to precipitate crystals. The crystals were collected by filtration, washed with water, dried under reduced pressure and then recrystallized from acetonitrile, thereby obtaining 22.3 g of 4-(4-hydroxyphenyl)-3-cyclohexen-1-ol. Purity: 99.1%. Purity-converted yield: 69.3% based on 4,4-bis(4-hydroxyphenyl)cyclohexanol.

Preparation of 4-(4-hydroxyphenyl)-cyclohexanol:

A four-necked glass flask was charged with 19.0 g (0.10 mole) of 4-(4-hydroxyphenyl)-3-cyclohexen-1-ol obtained as described above, 0.19 g of 5% palladium carbon and 200 ml of methanol. Under vigorous stirring, the resulting mixture was allowed to absorb hydrogen at 30°-35° C. under atmospheric pressure. After completion of the hydrogen absorption, the reaction mixture was aged for 15 minutes to complete the reaction.

After isolation and recovery of the palladium carbon by filtration, the methanol was distilled out by an evaporator so that 19.2 g of white crystals were obtained. 4-(4-Hydroxyphenyl)-cyclohexanol purified by gas chromatography had a purity of 99%. Its purity-converted yield was 99%. The overall yield was 58.2% based on 4-hydroxycyclohexanone.

What is claimed is:

1. Process for preparation of 4-(4-hydroxyphenyl)cyclohexanol, comprising catalytically reducing 4-(4-hydroxyphenyl)-3-cyclohexen-1-ol in the presence of an amount of hydrogeneffective to achieve said catalytic reduction and din the presence of a catalytically effective amount of at least one effective hydrogenation catalyst, said catalytic reduction being conducted at an effective temperature at which said catalytic reaction occurs, and said catalytic reaction being conducted at an effective pressure at which said catalytic reaction occurs.

2. The process as claimed in claim 1 wherein the hydrogenation catalyst is selected from the group consisting of Raney-nickel hydrogenation catalyst, reduced nickel hydrogenation catalyst, nickel hydrogenation catalyst, on a carrier, Raney-cobalt hydrogenation catalyst, reduced cobalt hydrogenation catalyst, cobalt hydrogenation catalyst on a carrier, Raney-copper hydrogenation catalyst, reduced copper hydrogenation catalyst, and copper hydrogenation catalyst on a carrier, palladium black hydrogenation catalyst, palladium oxide hydrogenation catalyst, colloidal palladium hydrogenation catalyst, palladium hydrogenation catalyst-carbon, palladium hydrogenation catalyst-barium sulfate, palladium hydrogenation catalyst-magnesium oxide, palladium hydrogenation catalyst-calcium oxide, palladium hydrogenation catalyst-alumina, platinum black hydrogenation catalyst, colloidal platinum hydrogenation catalyst, platinum oxide hydrogenation catalyst, platinum sulfide hydrogenation catalyst, platinum hydrogenation catalyst, carbon, colloidal rhodium hydrogenation catalyst, rhodium hydrogeneration catalyst-cardon, rhodium oxide hydrogenation catalyst, ruthenium hydrogenation catalyst, dirhenium heptoxide hydrogenation catalyst, rhenium hydrogenation catalyst-carbon, copper chromate hydrogenation catalyst, molybdenum oxide hydrogenation catalyst, vanadium oxide hydrogenation catalyst, and tungsten oxide hydrogenation catalyst and silver hydrogenation catalyst.

3. The process as claimed in claim 1 wherein the carrier for said nickel hydrogenation catalyst is selected from the group consisting of diatomaceous earth, alumina, pumice, silica gel and acid clay.

4. The process as claimed in claim 1 wherein said hydrogenation catalyst is selected from the group consisting of Raney-nickel hydrogenation catalyst and palladium hydrogenation catalyst-carbon.

5. The process as claimed in claim 1 wherein the catalytic reduction is conducted at a hydrogen pressure in a range of from atmospheric pressure to 5 kg/cm²G and a temperature in the range of 0° to 100° C.

6. The process as claimed in claim 1 wherein said hydrogenation catalyst is present in an amount of 0.0001 to 0.1 gram atom as the metal element or elements of the catalyst per mole of 4-(4-hydroxyphenyl)-3-cyclohexen-1-ol.

* * * * *